United States Patent [19]

Kaneko et al.

[11] Patent Number: 4,986,832
[45] Date of Patent: Jan. 22, 1991

[54] ARTIFICIAL BLOOD VESSEL AND PROCESS FOR PREPARING IT

[75] Inventors: Noriaki Kaneko; Yoshimi Hirata; Masahiro Moriwaki, all of Yokohama, Japan

[73] Assignee: Ube Industries, Ltd., Ube, Japan

[21] Appl. No.: 236,547

[22] Filed: Aug. 25, 1988

[30] Foreign Application Priority Data

| Sep. 4, 1987 | [JP] | Japan | 62-220351 |
| Sep. 4, 1987 | [JP] | Japan | 62-220352 |
| Sep. 4, 1987 | [JP] | Japan | 62-220353 |

[51] Int. Cl.$^5$ .............................. A61F 2/06
[52] U.S. Cl. ...................................... 623/1
[58] Field of Search .............. 623/1, 2, 7, 8, 11, 623/12, 66, 901; 264/41

[56] References Cited

U.S. PATENT DOCUMENTS

| 4,576,608 | 3/1986 | Homsy | 623/8 |
| 4,657,544 | 4/1987 | Pinchuk | 623/1 |
| 4,813,966 | 3/1989 | Gilding et al. | 623/1 |
| 4,822,352 | 4/1989 | Joh et al. | 623/66 |

FOREIGN PATENT DOCUMENTS

| 0130401 | 1/1985 | European Pat. Off. |
| 57-81349 | 5/1982 | Japan |
| 57-150954 | 9/1982 | Japan |
| 60-2257 | 1/1985 | Japan |
| 60-188165 | 9/1985 | Japan |
| 2092894 | 8/1982 | United Kingdom |

Primary Examiner—David J. Isabella
Attorney, Agent, or Firm—Frishauf, Holtz, Goodman & Woodward

[57] ABSTRACT

Disclosed is an artificial blood comprising a vessel wall that is comprised of plural layers and is porous as a whole, wherein an innermost layer has open-cell structure in which pores are connected through each other, and has a thickness of not less than 5 μm or more and not more than ⅔ of the thickness of the vessel wall. Also disclosed is a process for preparing an artificial blood vessel, comprising the steps of; solidifying a layer that has been formed on the surface of a rod-like substrate by coating a solution comprising a polymeric compound, followed by desolvation to make a rod; coating a solution having the same composition as the solution comprising a polymeric compound, on the inner surface of the rod, and spraying a powder which is insoluble to the polymeric compound solution thereon; solidifying the polymeric compound solution coated on the inner surface of the rod, followed by desolvation; and removing the powder from the polymeric compound.

10 Claims, 1 Drawing Sheet

ARTIFICIAL BLOOD VESSEL AND PROCESS FOR PREPARING IT

BACKGROUND OF THE INVENTION

This invention relates to an artificial blood vessel comprising a vessel wall that is porous as a whole, having an innermost layer capable of maintaining a long-term patency, having a property of being readily pierced with a suturing needle, and having durability to repeated needling, being free of permeation of blood from the vessel wall; and a process for preparing the same.

Transplantation of an artificial blood vessel to a living body causes initial thrombi on the inner surface that comes in contact with blood, and cells propagate themselves thereon to form a neointima, which becomes an antithrombotic intimal tissue. Thus, the artificial blood vessel can not play a role as a living body substitute before the inner wall of the blood vessel turns to part of the living body.

For this purpose, there is an artificial blood vessel in which an innermost layer of the inner surface side has been made porous so that such an intima can be effectively formed (Japanese Unexamined Patent Publication No. 22571/985).

However, even though the innermost layer is made porous, formed on the inner surface are nothing more than mere concaves if its pores are of mutually closed structure. This may result in a lowering of the tissue coaptation between the inner surface and intimal tissues or granulation tissues. In particular, the peeling-off of granulation tissues at an anastomosed portion may result in further growth of the granulation tissues to bring about excessive formation thereof (i.e. panni), thus causing obturation of a blood vessel at that part.

As stated above, the artificial blood vessel in which the innermost layer of the inner surface side has been merely made porous can not maintain a long-term patency because of weakness in the tissue coaptation, and any blood vessels having an inner diameter of 6 mm or less, particularly 4 mm or less, have been unable to be put into practical use.

The artificial blood vessel is also required, in view of readiness in operations, to have a property of being readily pierced with a suturing needle when anastomosed to a living body blood vessel. On the other hand, needling is so frequently repeated in blood access for use in blood dialysis, which is used in connecting arteries and veins, that the vessel wall is required to be durable to repeated needling, and also impermeable to blood so that there may be produced no hematoma or seroma (serum tumor) accompanying bleeding after needling.

Here, what is meant by "impermeable to blood" is that application of inner pressure of 450 mmHg to an artificial blood vessel may not result in permeation of plasma.

Available as an artificial blood vessel that may satisfy such a requirement is the one disclosed in Japanese Unexamined Patent Publication No. 150954/1982. This artificial blood vessel, however, has a dense layer, homogeneous and containing no vacuoles of at least 0.1 $\mu$m or more in diameter, obtained by coating a solution of a polymeric compound on a rod-like mold followed by drying and then desolvation.

For this reason, its vessel wall becomes rigid, and, even when its layer has a thickness, for example, of about 5 $\mu$m, extremely impedes the passing-through of a suturing needle to make it difficult to carry out an operation. As a result, the bleeding tends to stop with difficulty owing to repeated needling, causing generation of seromas, or resulting in protrusion of a cut-end surface of a living body blood vessel to the lumen side of the part anastomosed to a living body blood vessel to cause growth of panni. Disturbance at the inside may also cause a turbulent flow and partial stagnation of blood, causing the formation of thrombi.

Accordingly, in order to suppress the obturation due to the initial thrombi formed on the inside after transplantation, it is important for the vessel wall not only to be made of a antithrombotic material but also not to have such a dense layer.

Moreover, such a dense layer should preferably not exist also in order to suppress the obturation of a lumen caused when the artificial blood vessel is folded, i.e., the kinking.

As mentioned above, in the conventional artificial blood vessels, nothing has been available that has a property of being readily pierced with a suturing needle, has durability to repeated needling, and yet has a superior non-permeability to blood.

As a method of preparing an artificial blood vessel comprising a porous vessel wall, disclosed, for example, in Japanese Unexamined Patent Publications No. 81349/1982 and No. 1,881,651,985 is a method in which a material solution obtained by previously mixing and dispersing a pore-forming agent in a polymeric compound is formed and thereafter said pore-forming agent is removed. However, this conventional method, in which the pore-forming agent is used, has the following problems.

First, when the pore-forming agent is added in an excessively small amount, the vessel wall can not be made porous and only formed with unevenness on the surface because of the pore-forming agent remaining unremoved even by removing operation. On the other hand, when the pore-forming agent is add in an excessively large amount (e.g. an amount of more than 30 to 40% based on the weight of the polymeric compound), the mixed solution loses its fluidity, thus not only making it difficult to carry out forming treatment or surface treatment, but also resulting in cracks formed on the surface of the resulting artificial blood vessel or unevenness in thickness. In such an occasion, even if it is attempted to forcibly add 50% by weight of the pore-forming agent, there can be achieved a porosity of usually from 0.5 to 0.7 in approximation at best, which porosity is determined by the formula: apparent density/density of raw material (hereinafter the porosity is calculated in the same manner).

If it is attempted to solve the above problem by mixing the pore-forming agent in an amount of about 20% by weight, the pore-forming agent and the polymeric compound can not be uniformly dispersed, so that there can be formed only a product having a non-uniform pore distribution in the resulting vessel wall.

As discussed above, the conventional methods employing the pore-forming agent can not obtain artificial blood vessels having uniform porous structure, particularly artificial blood vessels of open-cell structure.

SUMMARY OF THE INVENTION

Accordingly, an object of this invention is to provide an artificial blood vessel of porous structure, having a high tissue coaptation, capable of suppressing the growth of panni or hypertropic thickening of intimas to give a superior long-term patency, and capable of being used for a long period of time; and a process for preparing the same.

The present inventors have made studies noting that the above fact that merely making the innermost layer to have the porous structure can bring about only insufficiency. As a result, they found the fact that making the innermost layer to have the open-cell structure in which pores in the layer are connected through each other can enhance the tissue coaptation because of penetration of intimal tissues or granulation tissues into this layer.

Moreover, they also found that even if the innermost layer has the open-cell structure, an excessively small thickness thereof results in a weak tissue coaptation, causing the obturation of blood vessel because of the growth of panni as mentioned above, and, on the other hand, an excessively large thickness results in hypertropic thickening of initial thrombi or neointimas to make it difficult to maintain the long-term patency, bringing about insufficiency in nutrient supply to intimal tissues positioned at the inside of intimas, i.e., the outer surface side of a blood vessel, to cause separation of intimas owing to necrocytosis.

As a result of studies repeated on the bases of these findings, they consequently found that making the innermost layer to have the open-cell structure and at the same time have a thickness within a given range makes it possible to give an artificial blood vessel having a high coaptation of tissues such as intimas, thus having accomplished this invention.

Namely, the artificial blood vessel of this invention comprises a vessel wall that is porous as a whole, wherein an innermost layer has open-cell structure in which pores are connected through each other, and has a thickness of not less than 5 $\mu$m and not more than $\frac{2}{3}$ of the thickness of the vessel wall.

In another aspect, they found that for solving the above problems involved in the conventional artificial blood vessels, the innermost layer on the inner surface side must have an open-cell structure having a high tissue coaptation with intimal tissues or the like in order to maintain the long-term patency, and that an intermediate layer contiguous to said innermost layer must have a closed-cell structure in which pores are closed independently from each other in order to prevent the vessel wall from turning rigid, prevent the intimal tissues from dying at the inside (deep part) (i.e., the outer surface side) of the open-cell structure, and further improve the property of being pierced with a suturing needle and at the same time retaining the impermeability to blood.

Thus, forming the intermediate layer of closed-cell structure on the part contiguous to the above innermost layer enables improvement in the property of being pierced with a suturing needle and the durability to repeated needling.

They also found that in order to make an artificial blood vessel to have homogeneous porous structure, a good result can be obtained when a solution of a polymeric compound that forms the vessel wall is coated on the surface of a substrate to form a polymeric compound layer and then a pore-forming powder is sprayed on the surface of this polymeric compound layer. More specifically, they found that spraying such a powder allows the polymeric compound solution to penetrate into the spaces between particles of the powder by capillary action of capillarity, so that the homogeneous porous structure can be obtained, thus having accomplished the preparation process of this invention.

Namely, the process for preparing an artificial blood vessel of this invention comprises the steps of;
  solidifying a layer that has been formed on the surface of a rod-like substrate by coating a solution comprising a polymeric compound, followed by (or removal of solvent) to make a rod;
  coating a solution having the same composition as said solution comprising a polymeric compound, on the inner surface of said rod, and spraying a powder thereon;
  solidifying said polymeric compound solution coated on the inner surface of the rod, followed by desolvation; and
  removing said powder from the polymeric compound.

DESCRIPTION OF THE PREFERRED EMBODIMENTS

Figure 1:
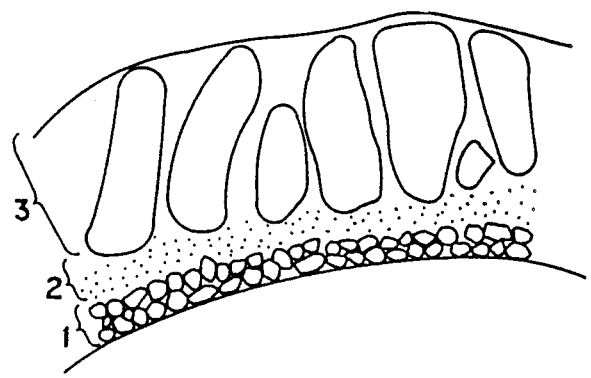
FIG. 1 is a partial sketch of a microscope photograph taken on a cross section of the vessel wall of an artificial blood vessel showing an embodiment of this invention.

The artificial blood vessel of this invention comprises a vessel wall comprising plural layers and having porous structure as a whole. In particular, the innermost layer thereof is a portion pertaining to its joining to intimal tissues or granulation tissues, influencing the tissue coaptation.

This innermost layer is required to have an open-cell structure comprising open pores connected through each other, have a thickness of not less than 5 $\mu$m and not more than $\frac{2}{3}$ of the thickness of the vessel wall. However, it may preferably have a thickness of not less than 20 $\mu$m in order to endure repeated needling when, for example, the artificial blood vessel is used as a blood vessel for use in blood dialysis. Here, when, for example, the artificial blood vessel is 4 mm in inner diameter and 0.4 mm in total thickness of the vessel wall, the innermost layer may preferably have a thickness ranging from 10 to 200 $\mu$m, more preferably from 20 to 100 $\mu$m.

This innermost layer comprises pores having an average diameter of from 5 to 150 $\mu$m and shapes of eggs or substantially elongated ovals, and/or modified shapes thereof, which are arranged in a most densely packed state, open toward the inner surface of the wall vessel with an average diameter of 5 to 150 $\mu$m, and have an open-cell structure in which adjacent pores are connected through each other with a hole having a diameter of at least 3 $\mu$m.

The above pores and the openings may preferably have an average diameter ranging from 5 to 150 $\mu$m. The average diameter otherwise less than this range makes it unable to suppress the granulation tissues growing out of a living body blood vessel at an anastomosed portion.

On the other hand, the average diameter otherwise more than 150 $\mu$m may result in enlarged unevenness on the inner surface of the vessel wall to bring about the difficulty that initial thrombi are produced in a large quantity after transplantation to cause obturation in a short period of time. Moreover, since the thickness of an initial thrombotic layer are proportional to the thickness of a neointima formed thereon after lapse of a long period of time, the inner diameter may become small after lapse of a long period of time until the vessel is finally obturated, even if there occurred no obturation in a short period of time.

Herein, the average diameter of the pores and the openings refers to an average value obtained by measuring maximum diameter of each pore and each opening in a field of view of 1.2 mm$^2$ given by taking a photograph at random with use of a scanning electron microscope of 1,000 magnification, and repeating the same operation 10 times.

The above procedures reveal that the open-cell structure of this innermost layer is substantially isotropic, and the cross section thereof shows the same appearance as the inner surface of the vessel wall when this layer has been cut in any direction at any position.

Hence, taking the open-cell structure in which the innermost layer has the above thickness brings about an enhanced coaptation with intimal tissues or the like after transplantation, thus making it possible to suppress the growth of panni or the hypertropic thickening of intimal tissues to prevent obturation of the blood vessel over a long period of time.

Also, making the porosity (bulk specific gravity/specific gravity of raw material) of this layer very high as much as from 0.90 to 0.99 enables ready penetration and growth of intimal tissues or the like.

On the other hand, the intermediate layer formed contiguous to said innermost layer and having the closed-cell structure comprises a number of independently closed pores of 0.01 μm or more in diameter, which closed pores play roles of enhancing the needle-pierceable properties of the artificial blood vessel and also regulating physical properties thereof, and may preferably have a diameter ranging from 0.1 to 100 μm, most preferably from 1 to 3 μm.

This is because the diameter of the closed pores otherwise greater than the value specified above (i.e. more than 100 μm) may result in a lowering of pressure resistance of the vessel wall to cause an increase in inner diameter owing to the creep that may occur with time after transplantation, or generation of minute pinholes. On the other hand, the diameter of the closed pores otherwise smaller than the value specified above (i.e., less than 0.01 μm) may make this layer so dense that the vessel wall may turn rigid.

This layer may preferably have a thickness ranging from 5 to 500 μm, particularly preferably from 50 to 300 μm. The thickness otherwise less than 5 μm may result in a lowering of the pressure resistance, making it impossible to maintain the blood impermeability as aimed in this invention, owing to the above-mentioned creep that may occur with time.

Preferred as component materials for the artificial blood vessel of this invention, comprising the innermost layer having the structure as described above, are materials having excellent adaptability to blood and tissues, i.e., polymers that has not any acute or chronic toxicity, heat build-up or hemolytic property and may not cause any inflammation on the surrounding tissues even when transplanted over a long period of time. Such polymers may include, for example, polyvinyl halides, polystyrene and derivatives thereof, polyolefin polymers, polyester condensates, cellulose macromolecules, polyurethane macromolecules, polysulfon resins and polyamide polymers.

There may be of course included copolymers or mixtures mutually containing any of these. Among these, preferred from the viewpoints of mechanical properties, stability in living bodies and also antithrombotic properties are those of polyurethane type. Specific examples thereof may include polyurethanes, polyurethaneureas, and a blend or interpenetration network structure of these with a silicone polymer. These also include segmented polyurethanes or polyurethaneureas, those containing polydimethylsiloxane in the backbone chain, and those containing fluorine in a hard or soft segment. In view of less possibility of suffering biodegradation, more preferred are polyurethanes or polyurethaneureas of polyether type than those of polyester type.

The polyether that constitutes the polyether segment of the above polyurethanes may most preferably include polytetramethylene oxide, but other polyalkylene oxides (provided that the alkylene moiety should have 2 and/or 3 carbon atoms) are also preferred. Specific example of such polyalkylene oxides may include polyethylene oxide, polypropylene oxide, and an ethylene oxide/propylene oxide copolymer or block copolymer. There may be also used polyurethanes containing a polytetramethylene oxide segment and a polyalkylene oxide (provided that the alkylene moiety should have 2 and/or 3 carbon atoms) in the same backbone chain and having both hydrophilic nature and mechanical properties. Such polyurethanes are more preferred as the component materials for the artificial blood vessel of this invention because of their antithrombotic properties and adaptability to living bodies that are far above the average.

The polyether that forms these soft segments may have a molecular weight usually ranging from 400 to 3,000, preferably from 450 to 2,500, and more preferably from 500 to 2,500. Among them, the best polyether segment includes polytetramethylene oxide chains having a molecular weight of from 800 to 2,500, particularly a molecular weight of from 1,300 to 2,000. If a molecular weight of more than 3,000, is used for this polyether soft segment this may result in poorness in the mechanical properties of polyurethane artificial blood vessels, and if a molecular weight of less than 400 is used, thus may result in so rigid a product that it can be of no use even if molded as an artificial blood vessel.

Synthesis of the polyurethanes may be carried out using a conventional method in which the above polyether terminated with hydroxyl groups at its both ends is reacted with a diisocyanate such as 4,4'-diphenylmethane diisocyanate, toluidine diisocyanate, 4,4'-dicyclohexylmethane diisocyanate or hexamethylene diisocyanate used in synthesis of known polyurethanes, to make an isocyanate-terminated prepolymer, which is then subjected to chain extension with use of a diamine such as ethylenediamine, propylenediamine or tetramethylene diamine, or a diol such as ethylene glycol, propylene glycol or butane diol.

The whole or innermost layer of the artificial blood vessel may also be formed with polyurethanes or polyurethane ureas containing an anticoagulant heparin, as in the artificial blood vessel disclosed in Japanese Unexamined Patent Publication No. 258670/1987. This effectively enables thin formation of initial thrombi particularly in an artificial blood vessel having an inner diameter of 4 mm or less, and hence can make thin also the thickness of a neointima after lapse of a long period of time.

In preparing the above artificial blood vessel, short fiber made of synthetic resin as exemplified by polyester, polypropylene, polyethylene, nylon and Teflon may further be mixed in the component materials. This effectively enables improvement of the strength as an artificial blood vessel, and particularly enables enhancement of the strength of the innermost layer pertaining to a joining to initial tissues or the like.

A solvent is used for making a solution by dissolving the above polymeric compound, where used is a good solvent, among which preferred is a solvent easy to handle or capable of being readily removed. It may include, for example, tetrahydrofuran, dioxane, acetone, dimethylformamide and diemthylacetamide. Such a solvent may also optionally be added and mixed with a bad solvent.

There is no particular limitation in the concentration of the polymeric compound solution so long as the polymeric compound layer can be formed, but it may usually range from 5 to 35% by weight, preferably from 5 to 25% by weight. This concentration in an excessively high range could make large the strength of the resulting artificial blood vessel, but may undesirably result in an excessively low penetration rate of the polymeric compound solution into the powder serving as a pore-forming agent. Also, the concentration in an excessively low range could make it able to obtain an artificial blood vessel having a sufficient thickness, but may undesirably result in a low strength.

Usable as the substrate used for forming thereon the polymeric compound layer are substrates made of materials insoluble to the solvent used, as exemplified by sheets, glass, every sort of metals and polymeric compounds. Shapes of such substrates can be appropriately selected depending on the shapes of intended artificial blood vessels.

Applicable as a method of forming the polymeric compound layer is a method in which a solution of the polymeric compound is coated on the surface of a mandrel.

After the polymeric compound layer was thus formed, the powder is adhered on the surface of the polymeric compound layer, which is then kept standing for a given time.

The powder is required to be insoluble in the polymeric compound solution and capable of being removed by separation from the polymeric compound. The powder is appropriately selected taking account of the porosity, pore size (or pore diameter) and shape of the artificial blood vessel to be obtained. For example, to enhance the porosity, there may be used the powder comprising particles having a regular and same shape and capable of being readily packed. This is because, when the powder was most densely packed, the porosity of the resulting vessel wall becomes higher with decrease in void.

Usable as the powder are water-soluble organic or inorganic salts as exemplified by sodium chloride, potassium chloride, calcium chloride, sodium sulfate, sodium carbonate and sodium acetate; water-soluble starch; casein; etc. Water-soluble starch is preferred among these since it is spherical, and also preferred since it can be sieved to make classification for use, to obtain a porous product having a desired pore size. Besides these, usable as the powder is a powder having a lower melting point than the polymeric compound used, in such a degree that it can be removed by heating, or a powder having so remarkably different chemical reactivity with the polymeric compound as to be capable of being removed by hydrolysis.

There is no particular limitation in methods of adhering the powder to the polymeric compound layer, but the powder may preferably be adhered so as to give a uniform thickness.

After the powder was adhered, it is kept standing for a given time until the polymeric compound solution penetrates into the powder by capillary action. Accordingly, the amount of the powder to be adhered (or thickness of a powder layer) depends on the amount of the polymeric compound solution to be penetrated.

The time for which it is kept standing may vary depending on the factors such as viscosity of the polymeric compound solution, ease of to wetting of the powder, and state in which the powder is packed. It ranges from several seconds to several minutes in usual cases.

Thereafter, the polymeric compound layer on which the powder has been adhered is kept in a solidifying medium together with the substrate to allow the polymeric compound layer to solidify.

Used as the solidifying medium used here are solvents sparingly soluble or insoluble to the polymeric compound and powder, but, besides these, also available are those having sufficient difference in the dissolving rate, or those by which the solidification of the solution can proceed in a sufficiently faster rate.

The time for which they are kept in the solidifying medium may vary depending on the types of the polymeric compound to be used and the solvent serving as the solidifying medium, but ranges from 1 to 24 hours in usual cases.

In place of such a solidifying step, there can also be applied a method in which the polymeric compound layer on which the powder has been adhered is dried. There is no particular limitation in the drying method in this occasion.

Subsequently, after separation of the solidified polymeric compound layer from the substrate, the powder is removed from the polymeric compound. This removing method may vary depending on the nature of the powder having been used. For example, when water-soluble starch was used as the powder, there can be applied a method in which the solidified polymeric compound layer is immersed in hot water of 50° C. or more for a given time or it is subjected to decomposition treatment by using amylase or diluted hydrochloric acid.

After the powder was removed, drying may be carried out, thus obtaining an artificial blood vessel whose vessel wall is porous as a whole. There is no particular limitation in the drying method in this occasion.

This invention will be described below in greater detail by giving Examples. In the following, "%" used on the ingredients of the component materials all indicates "% by weight". The attached drawings are partial sketches of microscope photographs with use of a microscope of 50 magnification taken on cross sections of vessel walls.

EXAMPLE 1

Polytetramethylene glycol terminated with hydroxyl groups at its both ends and having a molecular weight of 1,500 was reacted with 4,4'-diphenylmethane diisocyanate to obtain a prepolymer terminated with hydroxyl groups at its both ends. Next, butanediol was reacted with said prepolymer to obtain polyurethane (average molecular weight: $1.2 \times 10^4$). The resulting polyurethane was reprecipitated three times in total in a mixed solvent of a tetrahydrofuran-ethanol system to make purification.

Subsequently, the purified polyurethane was dissolved in a mixed solvent of 60% of dimethylamide and 40% of tetrahydrofuran to prepare a solution of 17% in polyurethane concentration. In the solution thus obtained, extruded in a constant rate from an orifice of 6 mm in diameter was a rod made of stainless steel and chromium-plated, having an outer diameter of 4 mm and a surface roughness of 0.3 μm in average, and set concentrically with said orifice. This operation resulted in adhesion of the polyurethane in a uniform amount on the whole peripheral surface of the rod from a space with a constant distance between the orifice and the rod made of stainless steel.

The extruded rod was immediately led into water of 35° C. and rapidly solidified from its outer side. Thereafter, the rod was kept standing in the water to remove the solvent from the polyethylene adhered on the rod, and then pulled up from water. The rod was pulled away, followed by washing and then drying at about 40° C. to obtain a porous, tubular product comprising polyurethane and having an inner diameter of 3.9 mm and an outer diameter of 5.4 mm.

The inner surface of the above tubular product was coated with a polyurethane solution having the same make-up with the above polyurethane solution, and an excess solution was removed with use of a suitable jig such as a squeezer of a piston type. Next, a solution obtained by mixing and dispersing soluble starch (particle diameter: 20 to 100 μm) and polyester short fibers of about 0.5 mm in length was sprayed on its inner surface, and left for 1 minute until the spaces between particles of the powder of starch was filled with the polyurethane solution by the action of capillarity, followed by solidification and desolvation in water. Thereafter, the resulting tubular product was treated for 3 hours with a hot water of 60° C. to remove the starch by dissolution, followed by washing with water and drying to obtain an artificial blood vessel having an innermost layer of open-cell structure in which pores are connected through each other.

This is the artificial blood vessel of this invention, which was 4 mm in inner diameter, 5 mm in outer diameter and 0.6 mm in thickness of the vessel wall, which vessel wall was porous as a whole as illustrated in FIG. 1.

The innermost layer 1 positioned on the inside of this artificial blood vessel was 80 μm in thickness and the pores gave the porosity of 97%.

This layer 1 was also comprised of polyester short fibers distributed at random, and minute pores that opened toward inner surface of the vessel wall with an average diameter of from 15 to 70 μm, where each pore was partitioned by fibrous or thin-sheet-like polyurethane. Observation of its cross section also confirmed that these pores were connected through each other with a hole having a diameter of 3 μm or more and the innermost layer 1 had the open-cell structure.

Also, the inside of this layer 1 had the same structure at every position.

On the outer side of the above layer 1, there existed an intermediate layer 2 of 5 to 10 μm in thickness, which contained a large number of mutually independent spherical closed pores of about 1 μm in diameter.

On the outer side of this intermediate layer 2, there further existed an outermost layer 3 comprising a group of large pores of from 200 to 300 μm in average diameter.

Here, the outermost layer 3 is the portion that imparts flexibility to the vessel wall, prevents kinking and contributes a joining to connective tissues.

In the above group of pores, each pore may desirably have a diameter of 1/5 or more of the thickness of the vessel wall and also range over the whole diametral direction of the layer, and the outer surface side may preferably be comprised of thin pore-wall films that are continuously formed as they stand.

Thus, making the innermost layer to have an open-cell structure enables improvement in the tissue coaptation on the inner surface, suppression of the growth of panni at a cut-end surface of a living body blood vessel or the hypertropic thickening of intimal tissues at the inner surface of the artificial blood vessel, thus bringing about remarkable improvement in the patency of the blood vessel.

Also, since the whole vessel wall is porous, the area coming in contact with a living body blood vessel can be made small at the cut-end surface of the artificial blood vessel to lessen stimulation by foreign body reaction, resulting in promotion of a cure of the living body blood vessel.

The lumen of this blood vessel was filled with cow blood and applied with an inner pressure of 450 mmHg for 48 hours, but no plasma passed through at all, showing that the vessel wall was impermeable to blood. The blood vessel used in the experiment was washed with a physiological saline and fixed with glutaraldehyde, which was used as a specimen to observe its cross section with use of a metal microscope. As a result, the blood did not enter the inside of the closed pores existing in the intermediate layer 2, and it was able to be confirmed that the blood vessel is impermeable to blood.

This artificial blood vessel with a length of 5 cm was transplanted to an iliac artery of an adult mongrel dog. Suturing was very readily performed and there was seen no bleeding from needle holes.

This blood vessel retained patency even after lapse of 8 months, showing that it was very good as an artificial blood vessel of a small caliber.

After 12 months, this blood vessel was removed to reveal that its outer surface was covered with connective tissues of about 1.5 mm in thickness to show perfect coaptation with the artificial blood vessel, which was not able to be peeled. The inner surface at the anastomosed part was connected to the living body blood vessel with smoothness, and the inner surface was completely covered with a thin intima with a thickness of from 0.1 to 0.2 mm. There was also seen no generation of pannus or thrombus.

Hence, because of its excellent patency, it differs from any conventional artificial blood vessels and can be used even for a blood vessel of 6 mm or less in caliber.

EXAMPLE 2

A porous tube made of polyurethane, having an inner diameter of 5 mm, was prepared in the same manner as in Example 1.

The resulting artificial blood vessel had an inner diameter of 5 mm, had a thickness of 0.8 mm in the whole vessel wall, and was porous.

The innermost layer of this artificial blood vessel had a thickness of from 80 to 120 μm, and the pores gave the porosity of from 96 to 98%. The above pores opened toward the wall inner surface with an average diameter of from 30 to 100 μm.

Observation on its cross section also revealed that inside this layer, fibrous polyurethanes with a thickness of from 2 to 10 μm were tangled with each other, polyester short fibers were distributed at random, and there was seen an open-cell structure in which adjacent pores were connected through each other.

On the outer side of this layer, there existed an intermediate layer having a thickness of about 80 μm and containing in its inside a large number of independently closed pores of from 1 to 3 μm in diameter, and on the outer side of the intermediate layer, there further existed an outermost layer having large pores with an average diameter of from 300 to 500 μm.

This blood vessel with a length of 8 cm was transplanted as a by-pass between a carotid artery and a cervical vein of an adult mongrel dog, and embedded subcutaneously.

After lapse of 3 weeks, a needle of 18 G (gauge) was pierced from the outside to have smoothly passed through the wall of the artificial blood vessel. The needle was kept remain unremoved for 4 hours and thereafter pulled out, but bleeding completely stopped after 10 seconds, showing a good hemostatic performance.

Subsequently thereafter, needling to this blood vessel was continued for 1 month at intervals of 5 times per day, but there occurred no hematoma or seroma, showing a superior performance as blood access for use in blood dialysis.

After 3 months, this blood vessel was taken out, and its state was observed to reveal that the connective tissues on the outer surface were toughly united to the artificial blood vessel. No pannus or thrombus was present also on the inner surface.

Figure 2:
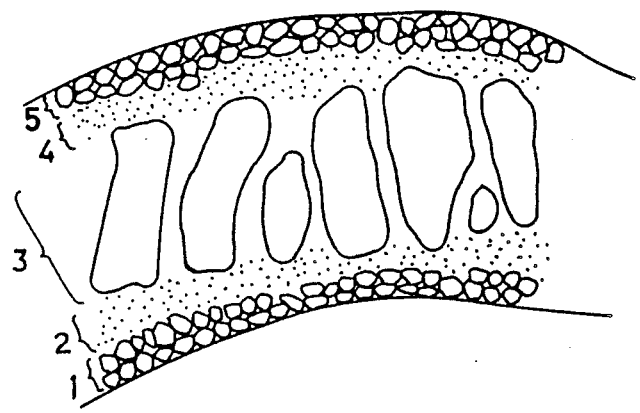
FIG. 2 is a partial sketch of the same in which the wall has a five layer structure.

The above both Examples describe artificial blood vessels of three-layer structure having on the inner surface of the blood vessel, the innermost layer having an open-cell structure, and the intermediate layer contiguous to this layer and having a closed-cell structure. However, needless to say, the artificial blood vessel may have a five-layer structure as illustrated in FIG. 2, in which in addition to the above inner surface structure the outermost layer 5 has the open-cell structure and the intermediate layer 4 contiguous to this layer 5 has the closed-cell structure.

The artificial blood vessel of this invention comprises an innermost layer having an open-cell structure and also having a thickness of not less than 5 μm or more and not more than ⅔ of the thickness of the vessel wall. Hence, it can achieve a superior tissue coaptation as compared with the artificial blood vessel whose inner surface is formed of mere concaves, and suppress the growth of panni or hypertrophic thickening of intimal tissues. Thus, even when used as an artificial blood vessel of 6 mm or less in inner diameter, particularly as an artificial blood vessel of 4 mm or less, it can exhibit an excellent long-term patency.

The artificial blood vessel of this invention has an intermediate layer contiguous to an innermost layer and having a closed-cell structure, so that it is an artificial blood vessel greatly advantageous in practical use as having an excellent long-term patency, having a property of being readily pierced with a suturing needle, showing blood impermeability against repeated needling, and having good durability.

Moreover, the preparation process of this invention makes it possible to prepare with ease and with good reproducibility an artificial blood vessel comprising a vessel wall having a wholly homogeneous, porous structure.

We claim:

1. An artificial blood vessel comprising a vessel wall that is comprised of two layers which have interfaces therebetween and wherein
   a porous innermost first layer has an open-cell structure in which the cells communicate with each other through interconnecting pores and has a thickness of at least 5 μm and not more than ⅔ of the total wall thickness of the vessel wall; and
   a second layer which is contiguous to said innermost layer, and has a closed cell structure which prevents blood from permeating therethrough, said closed cell structure comprising closed cells which do not communicate with each other or with the open cells of the innermost layer.

2. The artificial blood vessel according to claim 1, wherein said open-cell structure of the innermost layer is constituted of cells having an average diameter of from 5 to 150 μm and being substantially elongated ovals opening toward an inner surface of the vessel wall and said interconnecting pores having a diameter of at least 3 μm and connecting through each of these cells adjacent to each other.

3. The artificial blood vessel according to claim 1, wherein said second layer has a thickness of from 5 to 500 μm and is constituted of mutually independent closed pores having a diameter ranging from 0.01 to 100 μm.

4. The artificial blood vessel according to claim 2, wherein said second layer has a thickness of from 5 to 500 μm and is constituted of mutually independent closed pores having a diameter ranging from 0.01 to 100 μm.

5. The artificial blood vessel according to claim 1, wherein said vessel wall comprises a polyurethane and at least the innermost layer is reinforced with short fibers made of a synthetic resin distributed at random therein.

6. The artificial blood vessel according to claim 1, wherein said vessel wall comprises a polyurethaneurea and at least the innermost layer is reinforced with short fibers made of a synthetic resin distributed at random therein.

7. The artificial blood vessel according to claim 1, further comprising a third layer which is an outermost layer having a group of large pores of from 200 to 300 mm in average diameter to impart flexibility to the vessel wall, restrain kinking and contribute a joining to connective tissues.

8. The artificial blood vessel according to claim 7, wherein said open-cell structure of the innermost layer is constituted of pores having an average diameter of from 5 to 150 μm and being substantially elongated ovals and/or modified shapes thereof and opening toward an inner surface of the wall vessel with an average diameter of 5 to 150 μm, and interconnecting pores having a diameter of at least 3 μm and connecting through each of these pores adjacent to each other.

9. The artificial blood vessel according to claim 7, wherein said vessel wall comprises a polyurethane and at least the innermost layer is reinforced with short fibers made of a synthetic resin distributed at random therein.

10. The artificial blood vessel according to claim 7, wherein said vessel wall comprises a polyurethaneurea and at least the innermost layer is reinforced with short fibers made of a synthetic resin distributed at random therein.

* * * * *